(12) United States Patent
Pawlak et al.

(10) Patent No.: US 7,642,293 B2
(45) Date of Patent: *Jan. 5, 2010

(54) METHOD AND APPARATUS FOR PRODUCING METHANOL WITH HYDROCARBON RECYCLING

(75) Inventors: Nathan A Pawlak, Marquette, MI (US); Vladimir Ivanovich Vedeneev, Moscow (RU)

(73) Assignee: Gas Technologies LLC, Walloon Lake, MI (US)

( * ) Notice: Subject to any disclaimer, the term of this patent is extended or adjusted under 35 U.S.C. 154(b) by 31 days.

This patent is subject to a terminal disclaimer.

(21) Appl. No.: 11/351,532

(22) Filed: Feb. 10, 2006

(65) Prior Publication Data
US 2006/0154995 A1    Jul. 13, 2006

Related U.S. Application Data

(63) Continuation-in-part of application No. 11/319,093, filed on Dec. 27, 2005.

(51) Int. Cl.
| C07C 27/00 | (2006.01) |
| C07C 45/00 | (2006.01) |
| C07C 27/10 | (2006.01) |

(52) U.S. Cl. ............... 518/700; 518/703; 568/482; 568/910

(58) Field of Classification Search ............... 518/700, 518/703; 568/482, 910
See application file for complete search history.

(56) References Cited

U.S. PATENT DOCUMENTS

| 1,038,547 | A | 9/1912 | Fernekes |
| 1,500,080 | A | 7/1924 | Kloppenburg |
| 1,776,771 | A | 9/1930 | Boomer |
| 2,196,188 | A | 4/1940 | Bone et al. |
| 2,244,241 | A | 6/1941 | Bryce |
| 2,384,028 | A | 9/1945 | Hall |
| 2,467,993 | A | 4/1949 | Rossman |
| 2,722,553 | A | 11/1955 | Mullen |
| 2,922,809 | A | 1/1960 | Oberdorfer, Jr. |
| 3,027,411 | A | 3/1962 | Murphy |
| 3,130,026 | A | 4/1964 | Becker |

(Continued)

FOREIGN PATENT DOCUMENTS

EP    0 790 226    12/1996

(Continued)

OTHER PUBLICATIONS

"ASPECT Advanced Sustainable Processes by Engaging Catalytic Technologies—Call for Pre-proposals & Program Outline", Sep. 16, 2003, pp. 1-14.

(Continued)

*Primary Examiner*—Jafar Parsa
(74) *Attorney, Agent, or Firm*—Brooks Kushman P.C.

(57) ABSTRACT

An apparatus and method of producing methanol includes reacting a heated hydrocarbon-containing gas and an oxygen-containing gas in a reactor; to provide a product stream comprising methanol; and transferring heat from the product stream to the hydrocarbon-containing gas to heat the hydrocarbon containing gas. After removing methanol and $CO_2$ from the product stream, unprocessed hydrocarbons are mixed with the hydrocarbon containing gas fro reprocessing through the reactor.

29 Claims, 3 Drawing Sheets

U.S. PATENT DOCUMENTS

| | | |
|---|---|---|
| 3,145,220 A | 8/1964 | Bartok |
| 3,232,991 A | 2/1966 | Magee |
| 3,483,229 A | 12/1969 | Bernard |
| 3,689,575 A | 9/1972 | Tarhan |
| 3,718,006 A | 2/1973 | Ranke |
| 3,920,717 A | 11/1975 | Marion |
| 3,940,428 A | 2/1976 | Connell et al. |
| 3,975,172 A | 8/1976 | Ranke |
| 3,977,203 A | 8/1976 | Hinton et al. |
| 3,993,457 A | 11/1976 | Cahn et al. |
| 4,067,972 A | 1/1978 | Oswald et al. |
| 4,144,314 A | 3/1979 | Doerges et al. |
| 4,149,940 A | 4/1979 | Pinto |
| 4,152,407 A | 5/1979 | Fuchs |
| 4,203,915 A | 5/1980 | Supp et al. |
| 4,243,457 A | 1/1981 | Mayumi et al. |
| 4,243,613 A | 1/1981 | Brockhaus et al. |
| 4,252,548 A | 2/1981 | Markbreiter et al. |
| 4,271,086 A | 6/1981 | Supp et al. |
| 4,289,709 A | 9/1981 | Kaiser |
| 4,289,710 A | 9/1981 | Kaiser |
| 4,311,671 A | 1/1982 | Notman |
| 4,312,955 A | 1/1982 | Bartley |
| 4,324,567 A | 4/1982 | Ranke et al. |
| 4,346,179 A | 8/1982 | Sugier et al. |
| 4,353,712 A | 10/1982 | Marion et al. |
| 4,366,260 A | 12/1982 | Wainwright et al. |
| 4,374,288 A | 2/1983 | Scragg |
| 4,386,941 A | 6/1983 | Crouch et al. |
| 4,392,869 A | 7/1983 | Marion et al. |
| 4,394,137 A | 7/1983 | Marion et al. |
| 4,400,180 A | 8/1983 | Marion et al. |
| 4,430,316 A | 2/1984 | Ranke et al. |
| 4,443,560 A | 4/1984 | Le Blanc, Jr. et al. |
| 4,476,250 A | 10/1984 | Joyner et al. |
| 4,479,810 A | 10/1984 | Marion et al. |
| 4,490,156 A | 12/1984 | Marion et al. |
| 4,530,826 A | 7/1985 | Ohashi |
| 4,540,712 A | 9/1985 | Dombek |
| 4,564,643 A | 1/1986 | Shibata et al. |
| 4,575,387 A | 3/1986 | Larne et al. |
| 4,606,741 A | 8/1986 | Moreau et al. |
| 4,608,447 A | 8/1986 | Mazanec et al. |
| 4,609,388 A | 9/1986 | Adler et al. |
| 4,614,749 A | 9/1986 | Sapienza et al. |
| 4,618,732 A | 10/1986 | Gesser et al. |
| 4,619,946 A | 10/1986 | Sapienza et al. |
| 4,623,668 A | 11/1986 | Broecker et al. |
| 4,628,065 A | 12/1986 | Prouteau et al. |
| 4,628,066 A | 12/1986 | Bonnell et al. |
| 4,670,473 A | 6/1987 | Walker et al. |
| 4,721,458 A | 1/1988 | Conrad |
| 4,747,858 A | 5/1988 | Gottier |
| 4,760,210 A | 7/1988 | Sweeney |
| 4,782,096 A | 11/1988 | Banquy |
| 4,816,121 A | 3/1989 | Keefer |
| 4,822,393 A | 4/1989 | Markbreiter et al. |
| 4,861,360 A | 8/1989 | Apffel |
| 4,868,221 A | 9/1989 | Sie et al. |
| 4,873,267 A | 10/1989 | Sie et al. |
| 4,888,361 A | 12/1989 | Sie et al. |
| 4,982,023 A | 1/1991 | Han et al. |
| 5,012,029 A | 4/1991 | Han et al. |
| 5,015,798 A | 5/1991 | Han et al. |
| 5,063,250 A | 11/1991 | Murayama et al. |
| 5,067,972 A | 11/1991 | Hemmings et al. |
| 5,132,472 A | 7/1992 | Durante et al. |
| 5,177,279 A | 1/1993 | Harandi |
| 5,180,570 A | 1/1993 | Lee et al. |
| 5,220,080 A | 6/1993 | Lyons et al. |
| 5,384,335 A | 1/1995 | Tierney et al. |
| 5,496,859 A | 3/1996 | Fong et al. |
| 5,631,302 A | 5/1997 | Konig et al. |
| 5,735,936 A | 4/1998 | Minkkinen et al. |
| 5,770,630 A | 6/1998 | Kowal et al. |
| 5,861,441 A | 1/1999 | Waycuilis |
| 5,883,138 A | 3/1999 | Hershkowitz et al. |
| 5,886,056 A | 3/1999 | Hershkowitz et al. |
| 5,959,168 A | 9/1999 | Aalst et al. |
| 6,028,119 A | 2/2000 | Kokubu et al. |
| 6,102,987 A | 8/2000 | Gross et al. |
| 6,139,605 A | 10/2000 | Carnell et al. |
| 6,153,149 A | 11/2000 | Rabitz et al. |
| 6,159,432 A | 12/2000 | Mallinson et al. |
| 6,267,912 B1 | 7/2001 | Hershkowitz et al. |
| 6,300,380 B1 | 10/2001 | Kobayashi et al. |
| 6,328,854 B1 | 12/2001 | Sherman et al. |
| 6,342,091 B1 | 1/2002 | Menzel et al. |
| 6,447,475 B1 | 9/2002 | Castellano |
| 6,595,291 B1 | 7/2003 | Lia et al. |
| 6,625,988 B2 | 9/2003 | Weisenstein et al. |
| 6,632,971 B2 | 10/2003 | Brown et al. |
| 6,645,272 B2 | 11/2003 | Lemaire et al. |
| 6,667,347 B2 | 12/2003 | O'Rear et al. |
| 6,720,359 B2 | 4/2004 | O'Rear et al. |
| 6,726,850 B1 | 4/2004 | Reyes et al. |
| 6,736,955 B2 | 5/2004 | Shaw |
| 6,881,389 B2 | 4/2005 | Paulsen et al. |
| 6,881,758 B2 | 4/2005 | Guillard et al. |
| 6,942,719 B2 | 9/2005 | Stewart |
| 7,028,478 B2 | 4/2006 | Prentice, III |
| 7,067,558 B2 | 6/2006 | Grobys et al. |
| 7,071,238 B2 | 7/2006 | Gamlin et al. |
| 7,083,662 B2 | 8/2006 | Xu et al. |
| 7,108,838 B2 | 9/2006 | McGee |
| 2001/0006615 A1 | 7/2001 | Badano |
| 2002/0177741 A1 | 11/2002 | Allison et al. |
| 2003/0032844 A1 | 2/2003 | Seiki et al. |
| 2003/0065042 A1 | 4/2003 | Shaw |
| 2004/0065199 A1 | 4/2004 | Rojey et al. |
| 2004/0123523 A1 | 7/2004 | Rong et al. |
| 2004/0171701 A1 | 9/2004 | Shaw |
| 2006/0035986 A1 | 2/2006 | Bichkov et al. |
| 2006/0235088 A1 | 10/2006 | Olah et al. |
| 2006/0264683 A1 | 11/2006 | Knox et al. |

FOREIGN PATENT DOCUMENTS

| | | |
|---|---|---|
| GB | 2159153 A | 11/1985 |
| GB | 2196335 | 4/1988 |
| JP | 63001438 | 1/1988 |
| JP | 2004 315413 | 11/2004 |
| RU | 1336471 | 9/1996 |
| RU | 1469788 | 11/1996 |
| RU | 2162460 | 1/2001 |
| RU | 2 203 261 | 3/2002 |
| RU | 2200731 | 3/2003 |
| WO | WO 96/06901 | 3/1996 |
| WO | WO 03/031380 | 4/2003 |

OTHER PUBLICATIONS

G. Foulds, et al., "Kinetics, Catalysis, and Reaction Engineering—Homogeneous Gas-Phase Oxidation of Methane Using Oxygen as Oxidant in an Annular Reactor", Ind. Eng. Chem. Res. 1993, 32, pp. 780-787.

D.N. Koert, et al., A flow reactor for the study of homogeneous gas-phase oxidation of hydrocarbons at pressure up to 20 atm (2 MPa), Mar. 1992, 7 pgs.

E. Ranzi, et al., "A New Comprehensive Reaction Mechanism for Combustion of Hydrocarbon Fuels", Prepared for the Twenty-Fifth International Symposium on Combustion Jul. 31-Aug 5, 1994, Dec. 3, 1993, 23 pgs.

V. Arutyunov, "Recent Results on Fast Flow Gas-Phase Partial Oxidation of Lower Alkanes", Journal of Natural Gas Chemistry 13 (2004), 13 pgs.

M. M. Karaveav, et al. "Technology of Synthetic Methanol", Moscow, Chemistry, 1984 pp. 72-125.

E.V. Sheverdenkin, et al., "Kinetics of Partial Oxidation of Alkanes at High Ptessures: Oxidation of Ethane and Methane-Ethane Mixtures", Theoretical Foundations of Chemical Engineering, vol. 38, No. 3, 2004, pp. 311-315.

Zang, et al., "Recent Progress in Direct Partial Oxidation of Methane to Methanol", Journal of Natural Gas Chemistry. vol. 12, No. 2, 2003, pp. 81-89.

Burch, et al. "Direct Conversion of Methane into Methanol", J. Chem. Soc., Faraday Trans. 1, 1989, 85(10), pp. 3561-3568.

Lodeng, et al., "Experimental and Modeling Study of the Selective Homogeneous Gas Phase Oxidation of Methane to Methanol", Industrial Engineerng Chemical Res., 1995, pp. 1044-1059.

Henni, et al., "Solubility of Carbon Dioxide in Methyldiethanolamine + Methanol + Water", Journal of Chemical Engineering Data, 1995, 40, pp. 493-495.

R. Bhatnagar, et al., "Methane Conversion in AC Electric Discharges at Ambient Conditions", Plenum Publishing, NY, 1995, pp. 249-264.

C. Liu, et al., "Oxidative Coupling of Methane with AC and DC Corona Discharges", Industrial & Engineering Chemistry Research, vol. 35, No. 10, 1996, pp. 3295-3301.

A. Marafee, et al., "An Experimental Study on the Oxidative Coupling of Methane in a Direct Current Corona Discharge Reactor over $Sr/La_2O_3$ Catalyst", Industrial & Engineering Chemistry Research, vol. 36, No. 3, 1997, pp. 632-637.

C. Liu, et al., "Methane Conversion to Higher Hydrocarbons in a Corona Discharge Over Metal Oxide Catalysts with OH Groups", 1997, Applied Catalysis A: General 164, pp. 21-33.

D.W. Larkin, et al., "Oxygen Pathways and Carbon Dioxide Utilization in Methane Partial Oxidation in Ambient Temperature Electric Discharges", Energy & Fuels 1998, 12, pp. 740-744.

C. Liu, et al., "Nonoxidative Methane Conversion to Acetylene over Zeolite in a Low Temperature Plasma", Journal of Catalysis 179, 1998, pp. 326-334.

K. Thanyachotpaiboon, et al., "Conversion of Methane to Higher Hydrocarbons in AC Nonequilibrium Plasmas", AIChE Journal, Oct. 1998, vol. 4, No. 10, pp. 2252-2257.

C. Liu, et al., "Experimental Investigations on the Interaction Between Plasmas and Catalyst for Plasma Catalytic Methane Conversion (PCMC) over Zeolites", Natural Gas Conversion V, Studies in Surface Science and Catalysis, vol. 119, 1998, pp. 361-366.

C. Liu, et al., "Comparative Investigations on Plasma Catalytic Methane Conversion to Higher Hydrocarbons over Zeolites", Applied Catalysis A: General 178, 1999, pp. 17-27.

D.W. Larkin, et al., "Carbon Pathways, $CO_2$ Utilization, and In Situ Product Removal in Low Temperature Plasma Methane Conversion to Methanol", Greenhouse Gas Control Technologies, 1999, pp. 397-402.

C. Liu, et al., "Modification of $N_aY$ Zeolite in a Corona Discharge and its Application for the Reduction of Carbon Dioxide", Greenhouse Gas Control Technologies, 1999, pp. 1103-1105.

C.L. Gordon, et al., "The Production of Hydrogen From Methane Using Tubular Plasma Reactors", Advances in Hydrogen Energy, 2000, pp. 57-67.

D.W. Larkin, et al., "Production of Organic Oxygenates in the Partial Oxidation of Methane in a Silent Electric Discharge Reactor", Ind. Eng. Chem. Res. 2001, 40, pp. 1594-1601.

D.W. Larkin, et al., "Product Selectivity Control and Organic Oxygenate Pathways From Partial Oxidation of Methane in a Silent Electric Discharge Reactor", Ind. Eng. Chem. Res. 2001, 40, pp. 5496-5506.

T.A. Caldwell, et al., "Partial Oxidation of Methane to Form Synthesis Gas in a Tubular AC Plasma Reactor", Studies in Surface Science and Catalysis, vol. 36: Natural Gas Conversion VI, 2001, pp. 265-270.

C.L. Gordon, et al., "Selective Hydrogenation of Acetylene to Ethylene During the Conversion of Methane in a Catalytic DC Plasma Reactor", Studies in Surface Science and Catalysis, vol. 36: Natural Gas Conversion VI, 2001, pp. 271-276.

K. Supat, et al., "Synthesis Gas Production From Partial Oxidation of Methane with Air in AC Electric Gas Discharge", Energy & Fuels, 2003, 17, pp. 474-481.

K. Supat, et al., "Combined Steam Reforming and Partial Oxidation of Methane to Synthesis Gas Under Electrical Discharge", Ind. Engr. Chem. Res., 2003, 42, Page Est: 7.2 (A-H).

METHOD AND APPARATUS FOR PRODUCING METHANOL WITH HYDROCARBON RECYCLING

CROSS-REFERENCE TO RELATED APPLICATIONS

This application is a continuation-in-part of U.S. application Ser. No. 11/319,093 filed on Dec. 27, 2005. The disclosure of the above application is incorporated by reference.

BACKGROUND OF THE INVENTION

The present invention relates to a method of and an apparatus for producing methanol.

Methods and apparatuses for conversion of methane into methanol are known. It is known to carry out a vapor-phase conversion of methane into a synthesis gas (mixture of CO and $H_2$) with its subsequent catalytic conversion into methanol as disclosed, for example, in Karavaev M. M., Leonov B. E., et al "Technology of Synthetic Methanol", Moscow, "Chemistry" 1984, pages 72-125. However, in order to realize this process it is necessary to provide a complicated equipment, to satisfy high requirements to purity of gas, to spend high quantities of energy for obtaining the synthesis gas and for its purification, and to have a significant number of intermittent stages from the process. Also, for medium and small enterprises with the capacity less than 2,000 tons/day it is not efficient.

Russian Patent No. 2,162,460 includes a source of hydrocarbon-containing gas, a compressor and a heater for compression and heating of gas, a source of oxygen-containing gas with a compressor. It further includes successively arranged reactors with alternating mixing and reaction zones and means to supply the hydrocarbon-containing gas into a first mixing zone of the reactor and the oxygen-containing zone into each mixing zone, a recuperative heat exchanger for cooling of the reaction, mixture through a wall by a stream of cold hydrocarbon-containing gas of the heated hydrocarbon-containing gas into a heater, a cooler-condenser, a partial condenser for separation of waste gasses and liquid products with a subsequent separation of methanol, a pipeline for supply of the waste gas into the initial hydrocarbon-containing gas, and a pipeline for supply of waste oxygen-containing products into the first mixing zone of the reactor.

In this apparatus, however, it is not possible to provide a fast withdrawal of heat of the highly exothermic reaction of oxidation of the hydrocarbon-containing gas because of the inherent limitations of the heat exchanger. This leads to the necessity to reduce the quantity of supplied hydrocarbon-containing gas and, further, it reduces the degree of conversion of the hydrocarbon-containing gas. Moreover, even with the use of oxygen as an oxidizer, it is not possible to provide an efficient recirculation of the hydrocarbon-containing gas due to fast increase of concentration of carbon oxides in it. A significant part of the supplied oxygen is wasted for oxidation of CO into $CO_2$, which additionally reduces the degree of conversion of the initial hydrocarbon-containing gas and provides a further overheating of the reaction mixture. The apparatus also requires burning of an additional quantity of the initial hydrocarbon-containing gas in order to provide a stage of rectification of liquid products with vapor. Since it is necessary to cool the gas-liquid mixture after each reactor for separation of liquid products and subsequent heating before a next reactor, the apparatus is substantially complicated, the number of units is increased, and additional energy is wasted.

A further method and apparatus for producing methanol is disclosed in the patent document RU 2,200,731, in which compressed heated hydrocarbon-containing gas and compressed oxygen-containing gas are introduced into mixing zones of successively arranged reactors, and the reaction is performed with a controlled heat pick-up by cooling of the reaction mixture with water condensate so that steam is obtained, and a degree of cooling of the reaction mixture is regulated by parameters of escaping steam, which is used in liquid product rectification stage.

Other patent documents such as U.S. Pat. Nos. 2,196,188; 2,722,553; 4,152,407; 4,243,613; 4,530,826; 5,177,279; 5,959,168 and International Publication WO 96/06901 disclose further solutions for transformation of hydrocarbons.

It is believed that the existing methods and apparatus for producing methanol can be further improved.

SUMMARY

It is accordingly an object of the present invention to provide a method of and an apparatus for producing methanol, which is a further improvement of the existing methods and apparatuses.

It is another feature of the present teachings to provide a method of and an apparatus for producing methanol which can be used with minimal processing of gas and gas-condensate deposits, and also at any gas consumer, such as power plants, gas distributing and gas reducing stations, chemical production facilities, etc., or small methane producers, (i.e., coal mines, oil production (flares), landfills, farms.)

In keeping with these objects and with others which will become apparent hereinafter, one feature of the present invention resides, briefly stated, in a method of producing methanol, which includes the steps of supplying into a reactor a hydrocarbon-containing gas stream, supplying into the reactor an oxygen containing gas; carrying out in the reactor an oxidation of the hydrocarbon-containing gas by oxygen of said oxygen-containing gas; and, after removing impurities and products of the reaction, recycling un-reacted hydrocarbon gas into the hydrocarbon-containing gas stream for further reaction.

Another feature of the present teachings is an apparatus for producing methanol, which has a reactor for receiving and reacting a hydrocarbon-containing gas stream with an oxygen-containing gas, to carry out in the reactor oxidation of the heated hydrocarbon-containing gas by oxygen of said oxygen-containing gas. The apparatus also has a means for supplying into the reactor a cold hydrocarbon-containing gas to be mixed directly with a mixture of said heated hydrocarbon containing gas and said oxygen containing gas at a later stage of the reaction to inhibit the decomposition of formaldehyde. Un-reacted hydrocarbon gas is then processed to remove products and contaminants before being recycled back into the hydrocarbon-containing gas stream.

As can be seen, in accordance with the present teachings, a heated hydrocarbon-containing gas stream and oxygen-containing gas are supplied into a reaction zone or into a reactor, where a gas phase oxidation of the hydrocarbon-containing gas is performed at elevated temperature and pressure in the reaction zone. The reaction mixture is cooled before and is separated into waste gas and liquid product. The waste gas is scrubbed to remove $CO_2$ and returned to the heated hydrocarbon-containing gas stream. Cold hydrocarbon-containing gas is supplied into a regulation zone of the reactor to reduce the reaction temperature for example by 30-90° C. and thereby to provide a production and a redistribution of the ratio of products to produce corresponding quantities of methanol and formaldehyde.

In accordance with the present teachings, during cooling of the reaction mixture in the partial condenser, heat is transmitted to an input stream supplied into a formaldehyde rectification column for performing rectification of formaldehyde and simultaneous regeneration of the primary scrubber solvent, methanol. Within the partial condenser, dry gas is separated from raw liquids, including methanol, ethanol, and water. The raw liquids, through the flash drum, are supplied into a rectification column. The temperature of the top of the column is, between about 70 and about 75° C., the pressure in the column is, for example, up to 0.2 MPa. The final product is supplied to storage or further processing. The dry gas is scrubbed to remove $CO_2$ and formaldehyde and is then returned to the reactor in the hydrocarbon input stream.

The time of presence of the reaction mixture in the reactor is about 1.2 sec. The period of induction takes approximately 70% of this time, and thereafter a significant temperature increase of the mixture takes place. The content of methanol in the reacted gas is about 40% due to its high stability and selectivity, while the content of the formaldehyde is about 4% due to its lower stability and selectivity. In order to increase the portion of formaldehyde to 8-13% in the final product, the temperature of the reaction is reduced by 30-90° C. after the period of induction (after the formaldehyde has been formed) at 0.7-1.4 sec of reaction due to the injection of the cold hydrocarbon-containing gas into the regulating zone.

When the temperature of reaction is changed from 370° C. to 450° C., the content of aldehydes is increased from 5% to 13% and the content of organic acids is increased from 0.5% to 0.7%. The selectivity which is close to a maximum with respect to liquid organic products, including methanol and formaldehyde, is maintained using a concentration of oxygen in the initial gas mixture 2-2.8%.

The novel features which are considered as characteristic for the present invention are set forth in particular in the appended claims. The invention itself, however, both as to its construction and its method of operation, together with additional objects and advantages thereof, will be best understood from the following description of specific embodiments when read in connection with the accompanying drawings.

DESCRIPTION OF THE PREFERRED EMBODIMENTS

Figure 1A:
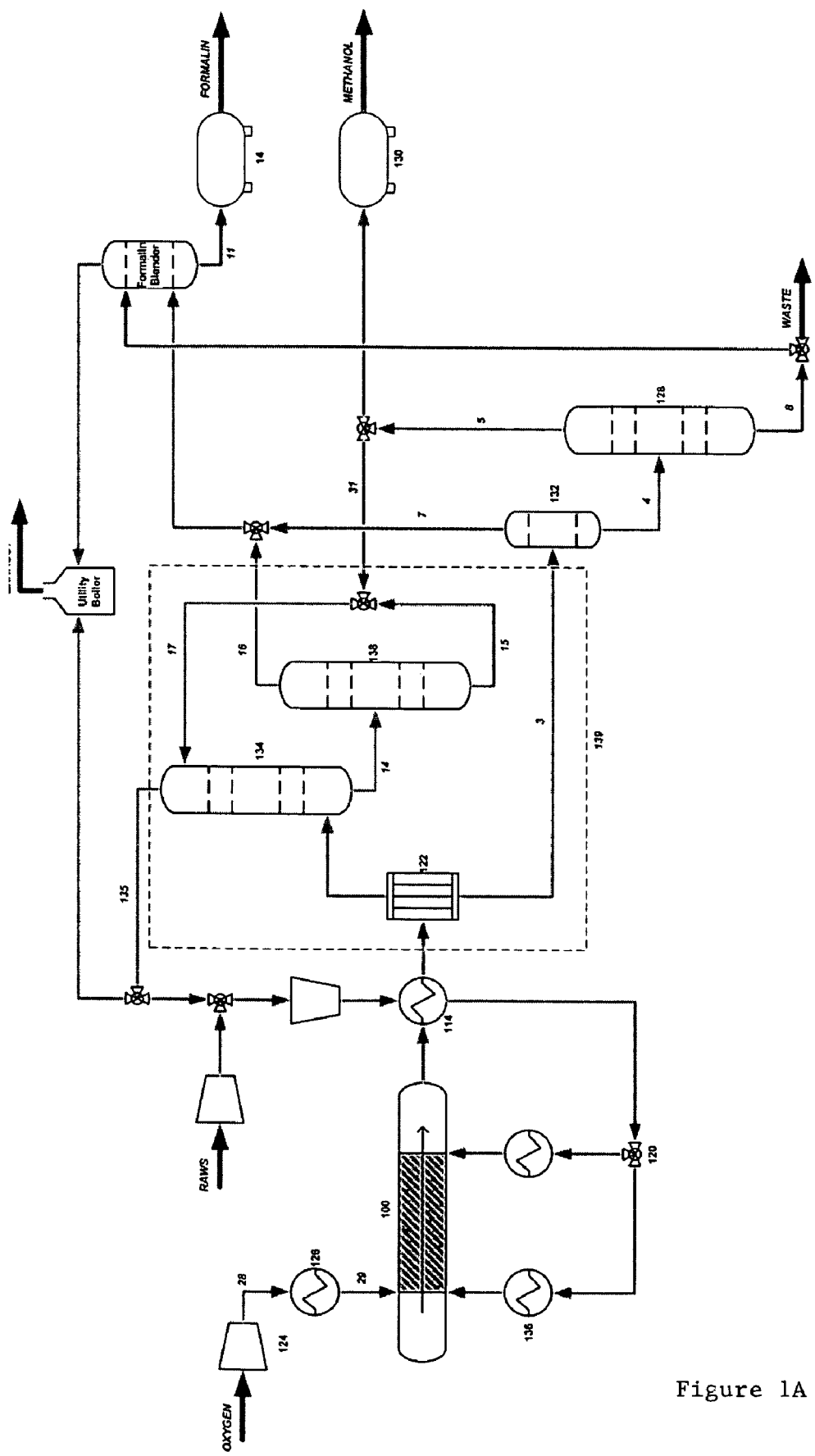
FIGS. 1A and 1B are views schematically showing a system of an apparatus for producing methanol in accordance with the present teachings.
Figure 1B:
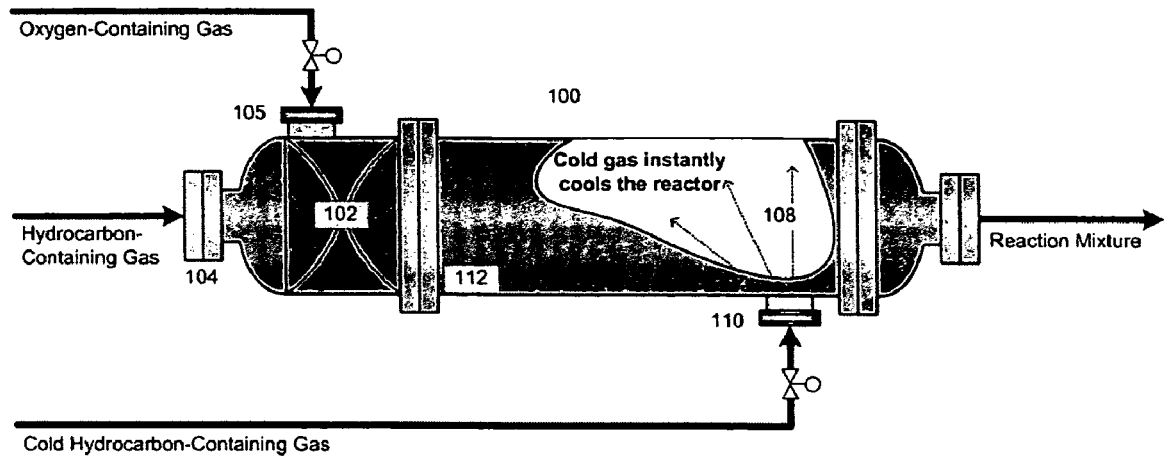

An apparatus for producing methanol in accordance with the present invention has a reactor 100 which facilitates a gas phase oxidation of a hydrocarbon-containing gas are shown in FIGS. 1A and 1B. FIG. 1B details the inputs and outputs of the reactor. The reactor 100 has a reaction zone 102 which is provided with a device 104 for introducing a heated hydrocarbon-containing gas stream and a device 105 for introducing an oxygen-containing gas. As explained in detail below, the oxygen-containing gas preferably has greater than 80% oxygen content to reduce the accumulation of inert gases due to the recycling process.

The reactor 100 further has a regulation zone 108 provided with an optional device 110 for introducing a cold hydrocarbon-containing gas stream for reducing the temperature of reaction during operation of the apparatus. In addition, the reactor 100 is provided with thermal pockets 112 for control and regulation of temperatures in corresponding zones, provided for example with thermocouples.

The apparatus has a device 114 for cooling the reaction mixture before separation. Additionally, the partial condenser 122 incorporates a gas-liquid heat exchanger to further reduce the temperature of the products. The condenser 122 separates $H_2O$ and alcohols from a hydrocarbon-$CO_2$ mixture. The partial condenser 122 is preferably isobaric, as opposed to isothermal, to avoid pressure losses. The product stream enters, and liquid stream and gaseous stream exit the condenser 122.

Block 139 represents equipment which is configured to separate contaminants and products from a hydrocarbon-containing recycle gas component. In this regard, the equipment 139 is configured to remove $CO_2$ from the reduced product stream. The equipment 139 can take the form of a purge valve, absorber, membrane separator, or an adsorber. It is envisioned the equipment 139 can be used to regulate the percentage of other non-reactive components such as $N_2$ with, for example, a purge valve.

In the event the system is configured to recover formaldehyde, the gaseous reduced product stream leaves the isobaric condenser 122 and is passed to the scrubber 134. The scrubber 134 prevents the accumulation of $CO_2$ and allows the physical capture of formaldehyde. The scrubber 134 can utilize a mixture of methanol and water to physically absorb formaldehyde and $CO_2$ from the hydrocarbon gas recycle loop 135. The efficiency of the scrubber 134, which can operate adequately without refrigeration, is made possible due to the high operating pressure of the recycle loop 135. This is opposed to cryogenically low temperatures utilized by traditional absorption processes. Other potential methods which can be utilized use materials such as various amines known to remove $CO_2$ and formaldehyde.

The gases enter the scrubber 134 as a "dirty" gas with some amount of formaldehyde and $CO_2$ present. These components will only be present in relatively dilute amounts, so the duty of the methanol absorbent is also relatively small. To fulfill the minimum absorption requirements, modification of the flow rate of methanol or operating temperature of the scrubber column can be used. If it is desirable to operate at extremely low absorbent flow rates, then a lower temperature can be utilized, for example 0° C. If it is desirable to operate at ambient temperatures or temperatures achievable via cooling water, then a high flow rate can be utilized, for example, ten times that of the flow rate for 0° C. In either scenario, the pregnant methanol absorbent stream 14 is completely regenerated by the formaldehyde distillation column 138. Optionally, the stream 14 from the scrubber 134 can be passed through the condenser 122 to provide cooling of the product stream and preheating of the methanol recycle to improve the energy efficiency of the formaldehyde distillation column 138.

The reactor 100 is connected with a compressor 124 and heater 126 for supply of compressed and heated oxygen-containing gas. The raw hydrocarbon-containing gas is mixed with cleaned hydrocarbon gas from the scrubber 134 and is heated using a heater 136. In the event the raw hydrocarbons have a high $CO_2$ content, the raw hydrocarbons can be mixed with the reduced product hydrocarbon stream from the condenser 122 prior to the entry of the scrubber 134 for removal of contaminant gases prior to entering the reactor.

The apparatus further has a unit for rectification of methanol which includes a flash drum 132, rectification column 128, and a vessel 130 from which methanol is supplied to storage or further processing. This rectification column 128 is used to separate methanol (light-key component) from ethanol (heavy-key component) and water (non-key component). As before, it is desirable for a portion of the heavy key to enter the distillate stream (as dictated by commercial specification for formalin). For methanol rectification, 99% or higher purity is typical and 99.999% is achievable with multiple columns. Stream 4 enters the column and the distillate, stream 5, and bottoms, stream 8, exit the column in liquid phase. Stream 8 has some amount of ethanol (and perhaps methanol, if ultra pure methanol was produced) and will be used as the basis of the aqueous makeup of the commercial formalin stream (stream 11). In this manner, some of the ethanol is recovered before the remainder is discarded in the liquid waste stream.

Disposed between the column 128 and the condenser 122 is a flash drum 132 for removal of $CO_2$ and formaldehyde from the liquid product stream. The purpose of the flash drum 132 is to drop the pressure to an appropriate level before entry into the methanol rectification column 128 and to substantially remove any dissolved gases, typically $CO_2$ and formaldehyde, from the liquid product stream.

In operation, the raw hydrocarbon-containing gas stream with a methane content for example up to 98% and the reduced hydrocarbon product stream are supplied from an installation for preparation of gas or any other source to the heater 136, in which it is heated to temperature 430-470° C. The heated hydrocarbon-containing gas is then supplied into the reaction zone 102 of the reactor 100. Compressed air with pressure, for example, of 7-8 MPa and with a ratio 80% to 100% and, preferably, 90% to 95% oxygen is supplied by the compressor 124 also into the reaction zone 102 of the reactor 100. Oxidation reaction takes place in the reaction zone 102 of the reactor 100. Between 2.0 and 3.0% $O_2$ of the total volume of the reactants are reacted with the heated hydrocarbon-containing gas stream as previously described. To limit the amount of $N_2$ within the system, for example to less than 30%-40%, or reduce the requisite size of the purge stream to achieve the same, the $O_2$ stream is preferably substantially pure, thus limiting the amount of $N_2$ entering the system. An optional second stream of cold or in other words a lower temperature hydrocarbon-containing gas than the gases in the reactor is supplied through the introducing device 108 into the regulation zone of the reactor 100. This stream is regulated by the regulating device 120, which can be formed as a known gas supply regulating device, regulating valve or the like. This cold stream can be composed of a raw hydrocarbon stream, a recycled stream, or a portion or combination of the two. The regulator is configured to adjust the volume or pressure of cold hydrocarbon-containing gas based on system parameters such as, but not limited to, pressure, temperature or reaction product percentages down stream in the system.

Depending on the intended mode of operation of the apparatus, in particular the intended production of methanol or methanol and formaldehyde, the reaction mixture is subjected to the reaction in the reactor without the introduction of the cold hydrocarbon-containing gas if it is desired to produce exclusively methanol. The introduction of the cold hydrocarbon containing gas is used when it is desired to produce methanol and formaldehyde. By introduction of the cold hydrocarbon-containing gas, the temperature of the reaction is reduced for example by 30-90° so as to preserve the content of formaldehyde into the separated mixture by reducing the decomposition of the formaldehyde to $CO_2$.

The reaction mixture is supplied into the heat exchanger 114 for transfer of heat to the reactor input stream from the reaction mixture exiting the reactor, and after further cooling is supplied within partial condenser 122. Separation of the mixture into high and low volatility components, (dry gas and raw liquid, respectively) is performed in the partial condenser 122 which may absorb at least some of the formaldehyde into the raw liquid stream as desired. The dry gas is forwarded to a scrubber 134, while the raw liquids from the condenser 122 are supplied to the flash drum 132.

The scrubber 134 functions to remove the $CO_2$ and formaldehyde from the dry gas stream. In this regard, the scrubber 134 uses both $H_2O$ and methanol at between 7-8 MPa pressure and between about 0° C. and about 50° C. to absorb $CO_2$ and formaldehyde. Once the $CO_2$ and formaldehyde are removed, the reduced stream of hydrocarbon gas is recycled by mixing the reduced stream with the raw hydrocarbon-containing gas stream either before or within the reactor, as desired. The raw hydrocarbon and reduced streams, individually or in combination, are then inputted into the reaction chamber 100 at input 104 or input 110 after being heated by heat exchanger 116 and heater 136 as previously described.

The rectification column is used to separate carbon dioxide (non-key component) and formaldehyde (light-key component) from methanol (heavy-key component) and water (non-key components). The pregnant methanol steam, stream 14, enters the rectification column and is separated into a formaldehyde distillate, stream 16, and a bottoms stream, stream 15. Some amount of methanol in the distillate stream is desirable since methanol is used as a stabilizer for the production of commercial grade formalin (6-15% alcohol stabilizer, 37% formaldehyde, and the balance being water). By allowing a portion of the heavy key into the distillate stream the separation is more easily achieved; furthermore, process losses typically experienced during absorbent regeneration are subsequently nullified as methanol within the distillate is used for formalin production. Stream 15 is supplemented by stream 31 so as to replace any methanol which was transferred to the distillate stream, stream 16. Combining stream 31 and stream 15 results in stream 17, which then returns to the scrubber 134 as regenerated methanol absorbent. Meanwhile, the formaldehyde distillate, stream 16, combines with the vapors from flash drum 132, stream 7, to form a mixture of formaldehyde, methanol, and carbon dioxide.

The formaldehyde, water, methanol and $CO_2$ removed by scrubber 134 are passed to formaldehyde rectification column 138. Column 138 removes formaldehyde and $CO_2$ from the methanol-water stream. Small amounts of methanol are combined with produced methanol and are inputted into the scrubber 134 to remove additional amounts of $CO_2$ and formaldehyde from the reduced hydrocarbon stream.

Free or non-aqueous formaldehyde is allowed to remain in the gas phase by operation of the isobaric condenser 122. The liquid methanol product stream, or raw liquids, would then comprise methanol, ethanol, and water by allowing formaldehyde to remain in the gaseous stream. In this case, the liquid stream exiting the isobaric condenser 122 can bypass the formaldehyde rectification portion of the process and enter the methanol rectification column after having optionally passed through the flash drum 132.

Figure 2:
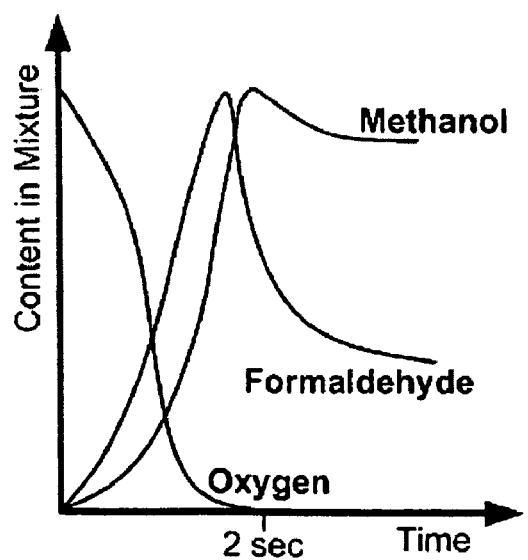
FIGS. 2 and 3 are views illustrating concentrations of oxygen, formaldehyde and methanol during reactions in accordance with the prior art and in accordance with the present invention correspondingly.
Figure 3:
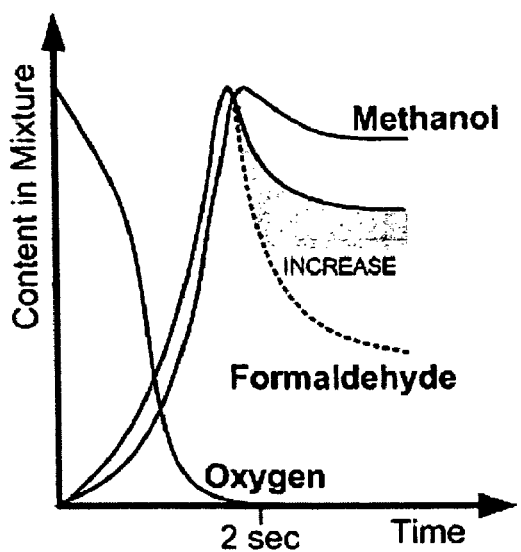

FIGS. 2 and 3 show diagrams of the concentration of oxygen, formaldehyde and methanol in reactions without cooling and with cooling, respectively.

As can be seen from FIG. 2, approximately after 2 sec, oxygen is burnt completely. At this moment the reaction temperature reaches its maximum and methanol and formaldehyde are produced with their proportions in the reaction mixture. Methanol is a more stable product at the end of the reaction and its concentration remains substantially stable after reaching its maximum concentration. Formaldehyde is less stable, and therefore with a temperature increase (the temperature increases until oxygen is burnt completely) its concentration somewhat reduces.

In the reaction with the cooling shown in FIG. 3, via the introduction of cold gas when the formation of methanol and formaldehyde is completed, the temperature of a final period of the reaction is reduced so as to inhibit the decomposition of formaldehyde.

Figure 4:
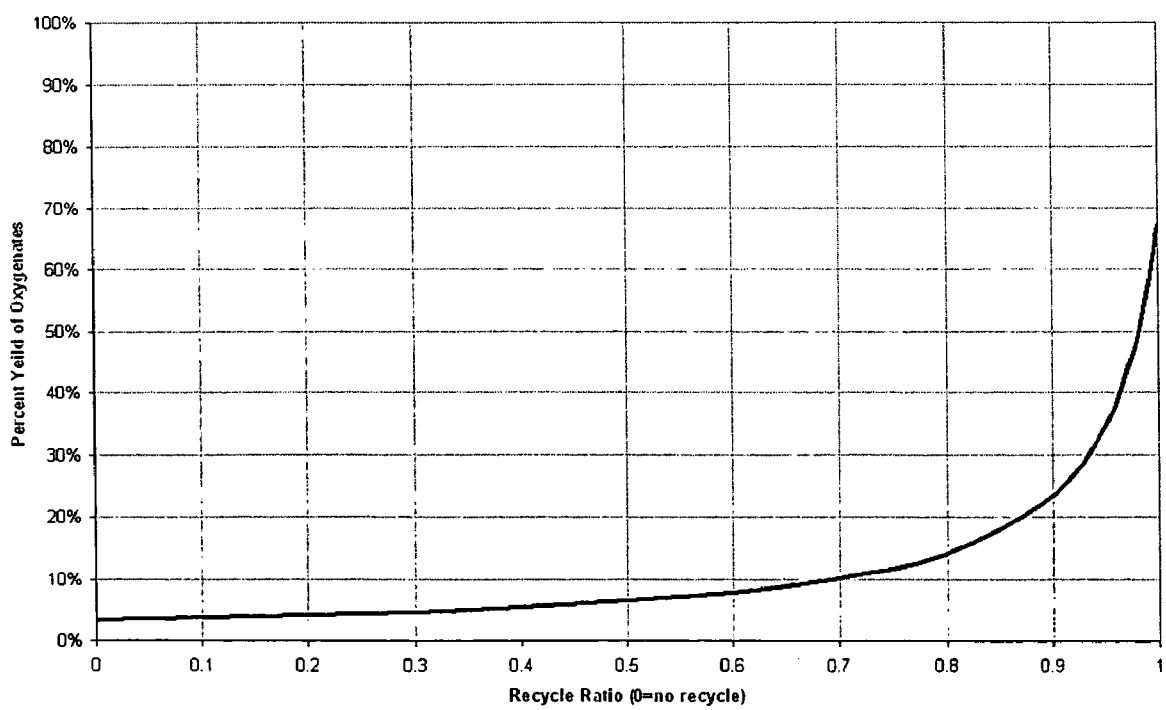
FIG. 4 represents a graph depicting the yield oxygenates of the system as a function of recycle ratio

FIG. 4 represents a graph depicting the yield of oxygenates for the system as a function of the recycle ratio of the recycling hydrocarbon gasses. Shown is a graph depicting the use of Michigan Antrim gas having 97% $CH_4$ and 1% $N_2$. In this regard, the graph shows a significant increase in product yield using the same input stream and with little increase in capital costs. As the system efficiently manages pressure and integrates process energy usage, energy requirements are minimized, thus increasing the overall system economics.

It will be understood that each of the elements described above, or two or more together, may also find a useful application in other types, of methods and constructions differing from the types described above.

While the invention has been illustrated and described as embodied in the method of and apparatus for producing methanol, it is not intended to be limited to the details shown, since various modifications and structural changes may be made without departing in any way from the spirit of the present invention.

Without further analysis, the foregoing will so fully reveal the gist of the present invention that others can, by applying current knowledge, readily adapt it for various applications without omitting features that, from the standpoint of prior art, fairly constitute essential characteristics of the generic or specific aspects of this invention. What is claimed as new and desired to be protected by Letters Patent is set forth in the appended claims.

What is claimed is:

1. A method of producing methanol, comprising:
supplying a first stream of heated hydrocarbon-containing gas into a reactor;
supplying into the reactor an oxygen-containing gas;
carrying out in the reactor oxidation of the first stream of heated hydrocarbon-containing gas by oxygen of the oxygen-containing gas to provide a product stream comprising methanol and formaldehyde; and transferring heat from the product stream to the first stream of heated hydrocarbon-containing gas after the reaction;
removing the methanol from the product stream; and
removing $CO_2$ from the product stream to form a reduced product stream comprising hydrocarbons by contacting with an absorbent, wherein the first stream comprises at least a portion of the reduced product stream.

2. The method as defined in claim 1 wherein the oxidation is partial oxidation without a catalyst.

3. The method as defined in claim 1 wherein the transfer of heat from the product stream to the first stream of heated hydrocarbon-containing gas at least partially heats the first stream of heated hydrocarbon-containing gas which is thereafter further heated to provide the first stream of heated hydrocarbon-containing gas.

4. The method as defined in claim 1, wherein heat is transferred from the product stream to the hydrocarbon-containing gas in a heat exchanger downstream of the reactor.

5. The method as in claim 4 wherein the heat exchanger portion of the reactor comprises a downstream portion of the reactor.

6. The method as in claim 1 wherein removing $CO_2$ is passing the product stream through at least one of a scrubber, a purge stream, or a membrane separator.

7. The method as in claim 1 where carrying out in the reactor oxidation occurs at pressures between about 7 and 8 MPA.

8. The method as in claim 1 wherein the oxygen-containing gas comprises between 80% and 100% oxygen.

9. The method as in claim 1 wherein the oxygen containing gas comprises less than 20% nitrogen.

10. The method as in claim 1 wherein the carrying out of oxidation in the reactor occurs at temperatures between about 430° C. and 470° C.

11. A method as defined in claim 1, further comprising supplying of the cold hydrocarbon-containing gas into the reactor.

12. The method as in claim 11 wherein said supplying of the cold hydrocarbon-containing gas into the reactor includes suppling the cold hydrocarbon-containing gas into the reactor at the state when formation of methanol and formaldehyde is substantially completed or thereafter.

13. A method as defined in claim 11, wherein said supplying of the cold hydrocarbon-containing gas includes adjusting the quantity of the cold hydrocarbon-containing gas so to influence the extent of the decomposition of formaldehyde in the reactor.

14. A method as in claim 11, wherein the cold hydrocarbon-containing gas is colder than the heated hydrocarbon-containing gas.

15. A method as in claim 1 wherein the absorbent comprises methanol.

16. A method of producing methanol, comprising:
supplying a first stream of heated hydrocarbon-containing gas into a reactor;
supplying into the reactor an oxygen-containing gas;
carrying out in the reactor oxidation of the heated hydrocarbon-containing gas stream by oxygen of the oxygen-containing gas to provide a product stream comprising methanol and formaldehyde; and transferring heat from the product stream to the first stream of heated hydrocarbon-containing gas after the reaction;
removing the methanol from the product stream; and
removing $CO_2$ under isobaric conditions from the product stream to form a reduced product stream comprising hydrocarbons, wherein the first stream comprises at least a portion of the reduced product stream.

17. The method as defined in claim 16 wherein the oxidation is partial oxidation without a catalyst.

18. The method as defined in claim 16 wherein the transfer of heat from the product stream to the hydrocarbon-containing gas at least partially heats the hydrocarbon-containing gas which is thereafter further heated to provide the first stream of heated hydrocarbon-containing gas.

19. The method as defined in claim 16, wherein heat is transferred from the product stream to the hydrocarbon-containing gas in a heat exchanger downstream of the reactor.

20. The method as in claim 19 wherein the heat exchanger portion of the reactor comprises a downstream portion of the reactor.

21. The method as in claim 16 wherein removing $CO_2$ is passing the product stream through at least one of a scrubber, a purge stream, or a membrane separator.

22. The method as in claim 16 where carrying out in the reactor oxidation occurs at pressures between about 7 and 8 MPA.

23. The method as in claim 16 wherein the oxygen-containing gas comprises between 80% and 100% oxygen.

24. The method as in claim 16 wherein the oxygen containing gas comprises less than 20% nitrogen.

25. The method as in claim 16 wherein the carrying out of oxidation in the reactor occurs at temperatures between about 430° C. and 470°C.

26. A method as defined in claim 16, further comprising supplying of the cold hydrocarbon-containing gas into the reactor.

27. The method as in claim 26 wherein said supplying of the cold hydrocarbon-containing gas into the reactor includes suppling the cold hydrocarbon-containing gas into the reactor at the state when formation of methanol and formaldehyde is substantially completed or thereafter.

28. A method as defined in claim 26, wherein said supplying of the cold hydrocarbon-containing gas includes adjusting the quantity of the cold hydrocarbon containing gas so to influence the extent of the decomposition of formaldehyde in the reactor.

29. A method as in claim 26, wherein the cold hydrocarbon-containing gas is colder than the heated hydrocarbon containing gas.

* * * * *